United States Patent

Koller et al.

[11] Patent Number: 5,720,750
[45] Date of Patent: Feb. 24, 1998

[54] DEVICE FOR THE PREPARATION OF A TUBULAR BONE FOR THE INSERTION OF AN IMPLANT SHAFT

[75] Inventors: Hansjörg Koller, Winterthur, Switzerland; Anne Tregoning Miller, Cambridge, United Kingdom

[73] Assignee: Sulzer Medizinaltechnik AG, Winterthur, Switzerland

[21] Appl. No.: 722,646

[22] Filed: Sep. 30, 1996

Related U.S. Application Data

[63] Continuation of Ser. No. 206,997, Mar. 7, 1994, abandoned.

[30] Foreign Application Priority Data

Apr. 7, 1993 [EP] European Pat. Off. ............ 93810252

[51] Int. Cl.$^6$ .................................................. A61B 17/56
[52] U.S. Cl. .................................................. 606/85
[58] Field of Search ........................ 606/85, 84, 81, 606/80, 79, 99, 101; 623/18, 22, 23

[56] References Cited

U.S. PATENT DOCUMENTS

| | | |
|---|---|---|
| 4,508,005 | 4/1985 | Herman . |
| 4,583,270 | 4/1986 | Kenna ........................... 606/85 X |
| 4,587,964 | 5/1986 | Walker et al. ................. 606/85 X |
| 4,921,493 | 5/1990 | Webb, Jr. et al. ............. 606/85 |
| 4,963,155 | 10/1990 | Lazzeri et al. ............... 623/23 |
| 5,002,581 | 3/1991 | Paxson . |
| 5,089,003 | 2/1992 | Fallin . |
| 5,342,362 | 8/1994 | Kenyon et al. ............... 606/79 |

FOREIGN PATENT DOCUMENTS

| | | |
|---|---|---|
| 0 122 670 | 10/1984 | European Pat. Off. . |
| 426.528 | 7/1911 | France . |
| 2 656 519 | 7/1991 | France . |
| 2 659 042 | 9/1991 | France . |
| WO 89/04238 | 5/1989 | WIPO . |

*Primary Examiner*—Guy V. Tucker
*Attorney, Agent, or Firm*—Townsend and Townsend and Crew LLP

[57] ABSTRACT

The device contains a rasp (2) corresponding to the implant shaft, which comprises a shaft body (4), which can be driven into the osseous tissue, and a neck part (5) protruding therefrom, which can be equipped with a test ball corresponding to the ball-and-socket joint, and a grip part (7) which can be coupled to the rasp (2) for the insertion and withdrawal of the shaft body (4). The grip part (7) contains a guide bush (10), which can be slipped onto the neck part (5), and a slip-on part (14) having a stop face which can be placed on a front support face of the neck part (5). On the grip part (7) is articulated a coupling part (11), which comprises a claw (27) which through a recess in the guide sleeve (10) can engage in a recess of the neck part (5) and can be disengaged from it. With this device, which can be manufactured from simple components which are easy to keep sterile, all stop, guide and clamping faces involved in the insertion and withdrawal of the shaft body (4) lie inside the enveloping shell face of the neck part (5) and as a result are protected from contact with fluid and bone particles.

17 Claims, 2 Drawing Sheets

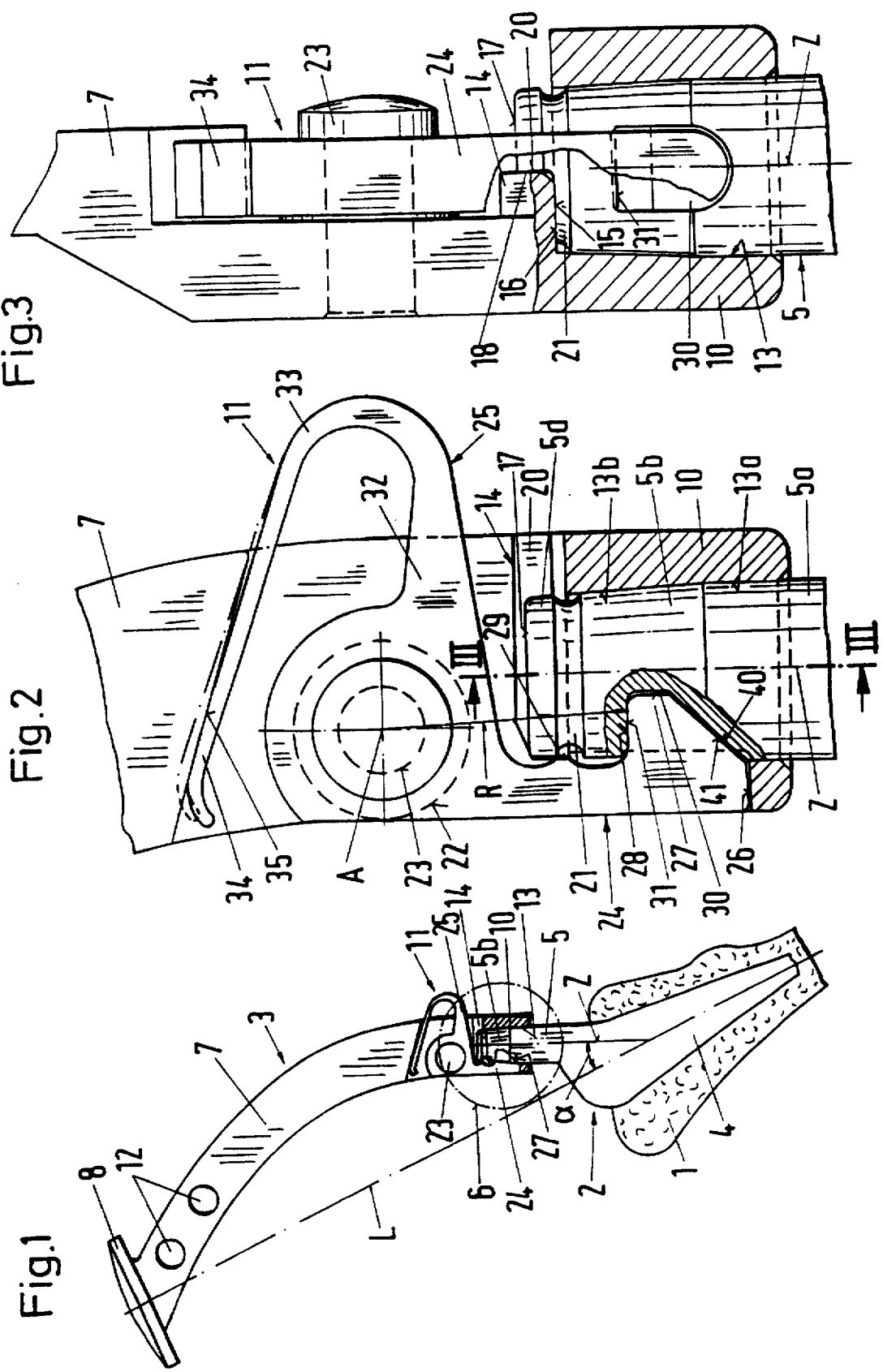

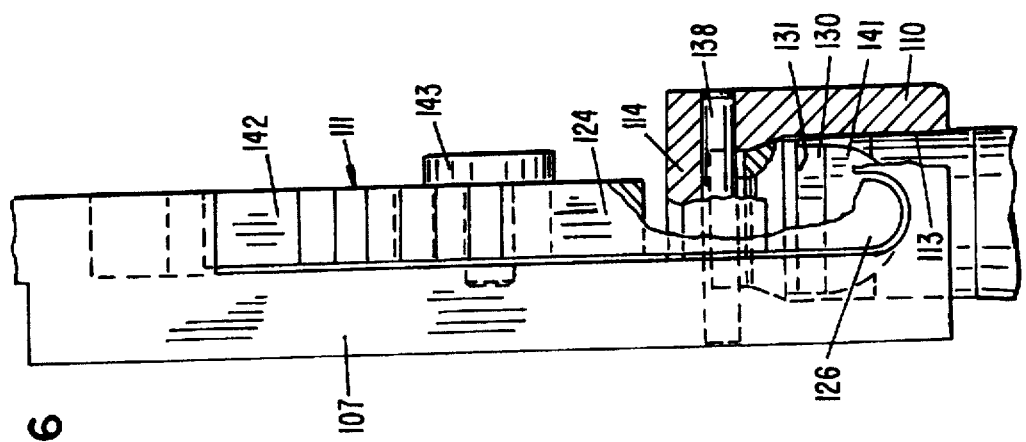
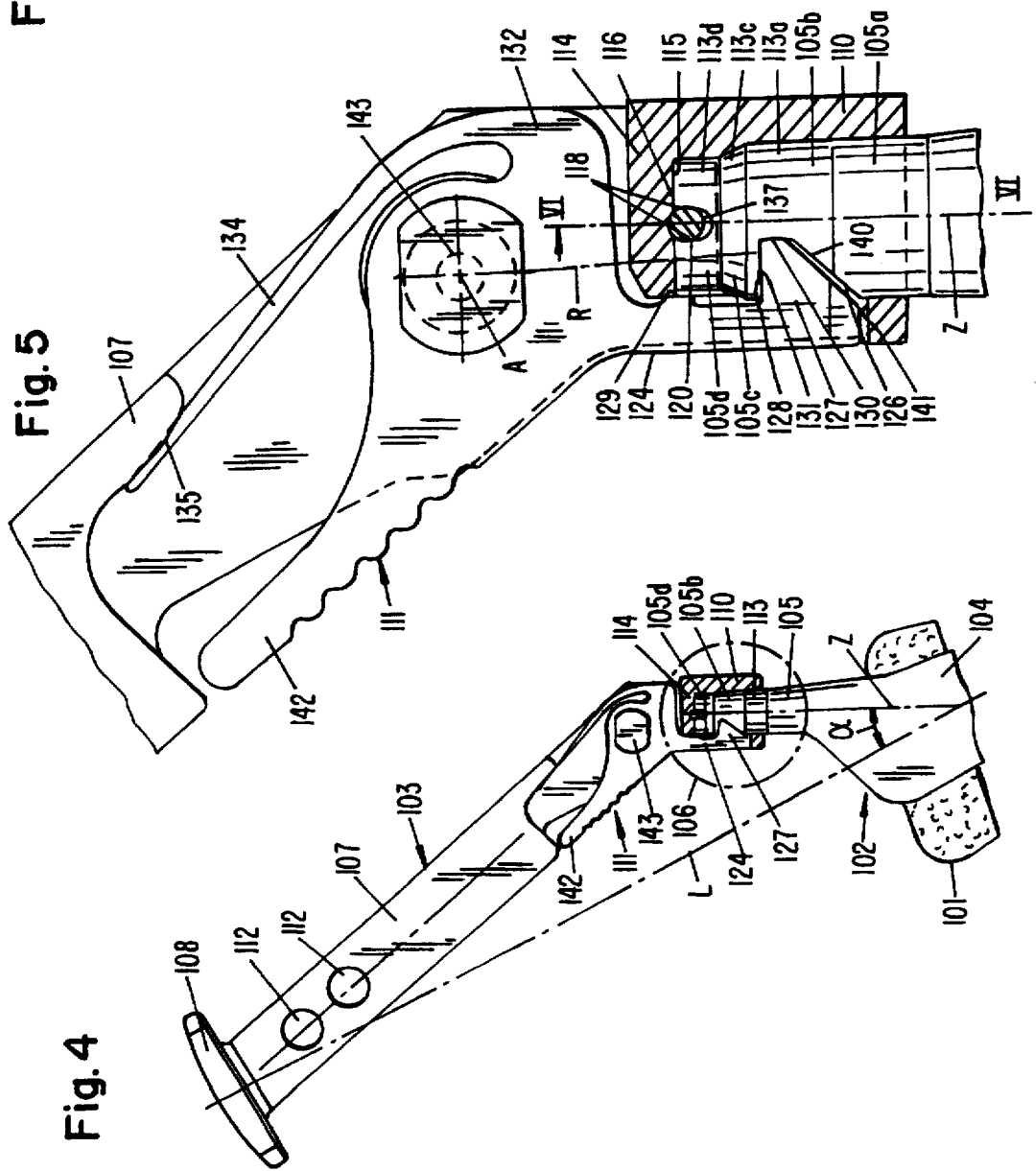

DEVICE FOR THE PREPARATION OF A TUBULAR BONE FOR THE INSERTION OF AN IMPLANT SHAFT

This is a continuation of application Ser. No. 08/206,997, filed Mar. 7, 1994, now abandoned, the disclosure of which is incorporated by reference.

BACKGROUND OF THE INVENTION

The invention relates to a device for the preparation of a tubular bone for the insertion of an implant shaft to be equipped with an artificial ball-and-socket joint, in particular a femur shaft of a hip joint prosthesis, having a rasp corresponding to the implant shaft with respect to shape and size, which comprises a shaft body which can be driven into and withdrawn from the bone in the direction of its longitudinal axis, and a neck part protruding therefrom which can be provided with a test ball corresponding to the ball-and-socket joint, and a grip part which can be placed on the rasp and which contains a guide bush having a bore to house the neck part and a locking mechanism which can be detachably connected to the neck part.

In a device of the known type described in German Patent Specification 36 01 928, the grip part is designed with a transversely extending flange which can be placed on the shaft member, and which contains an aperture to house a neck-shaped, cylindrical shaft portion and which on its side remote from the shaft body bears the locking mechanism. The known locking mechanism contains a sleeve-like support connected to the flange, into which the shaft portion protrudes, a spring disposed in the support and two stops which can be inserted into an annular groove in the shaft portion, and also a sleeve, which is movably held by the support with a spacing to the flange and to the grip part and is retained under the action of the spring in a position in which the two stops engage in the annular groove. To release the locking, the sleeve is to be moved in the axial direction of the support against the action of the spring and rotated into a position which permits the stops to be withdrawn from the annular groove of the neck-shaped shaft portion and the grip part to be removed. The known device contains a relatively large number of movable parts, which require a correspondingly large expenditure of labor and time during manufacture and during assembly and also during the cleaning and sterilization of the device.

SUMMARY OF THE INVENTION

The object of the invention is to create a device of the aforementioned type which has been developed further in this respect in particular, in a compact style which has been simplified in comparison with previous designs, which contains few components, which have a robust design and are easy to handle, and which guarantees that the implantation region can be prepared and kept clean with a correspondingly low expenditure of labor and time.

An important advantage of the design according to the invention lies in that the pressure to be applied to the front side of the neck part to drive in the rasp via the grip part, and thus on the point the furthest away from the osseous tissue, is transferred to the rasp, so that the grip part can be kept away from the shaft body and the osseous tissue and an unimpeded observation of the implantation region can constantly be guaranteed. A further advantage of the design according to the invention lies in that the guide bush is constructed directly at the end portion of the grip part close to the shaft body and can be connected thereto to form a handy, compact tool. The coupling part mounted on the grip part is easily accessible and enables the use of an adjustment arrangement, which has a simple construction and is easy to operate, to couple and uncouple the coupling part with or from the neck part. The device according to the invention is characterised by easy-to-manufacture and easy-to-assemble parts, which can be easily cleaned and sterilised.

The design enables in a simple manner and with a low expenditure of time a precise predetermination of the position of the ball-and-socket joint to be implanted with the use of test balls having conical faces extending with varying depths into the interior of the ball, so that with a set of test balls having, for example, penetration depths staggered by a few millimeters, even when the shaft body has been completely driven in, the test balls can be positioned at an appropriate distance from the shaft body dictated by the anatomical conditions, and on a trial basis can be brought together with the associated articular shell. By the positioning of the cylindrical and conical guide faces of the neck part, with respect to the support face constructed thereon and also of the guide faces of the bore of the guide bush with respect to the stop face constructed on the grip part, there can be achieved a precise guidance of the guide bush, which can be placed, with slight clearance, on the neck part. In addition, the guide bush is prevented from becoming fixed on the neck part and thus damage to the cone face of the neck part, which is essential for precisely positioning the test balls, is prevented.

BRIEF DESCRIPTION OF THE DRAWINGS

Further details and features become apparent from the following description of an exemplified embodiment of the invention represented diagrammatically in the drawings, in conjunction with the claims.

FIG. 1 shows a device constructed according to the invention for the preparation of a thigh bone, represented partially in a longitudinal section;

FIG. 2 shows a detail of the device shown in FIG. 1 in a corresponding partial view with a partial section; and in a larger representation and FIG. 3 shows a side view of the detail with a partial section along line III—III in FIG. 2;

FIG. 4 shows a further device constructed according to the invention according to an alternative embodiment; FIG. 5 shows a detail of the device according to FIG. 4 in a larger representation; and FIG. 6 shows a side view of the detail with a partial section along line VI—VI in FIG. 5.

DESCRIPTION OF THE PREFERRED EMBODIMENTS

The device according to FIG. 1 contains an evacuating instrument in the form of a rasp 2, which is intended to be driven into a tubular bone, and as shown in the representation, driven into a thigh bone 1, and an auxiliary tool 3, which can be connected to said rasp in a frictional and form-fit manner, to guide the rasp 2 when it is driven into the osseous tissue and when it is withdrawn from the osseous tissue. The rasp 2 is designed with a shaft body 4, which tapers conically in relation to its longitudinal axis L and can be driven into the osseous tissue, and a neck part 5 protruding therefrom, which comprises a cylindrical guide portion 5a and a conical guide portion (cone face) 5b, which tapers in relation to a central axis Z. As represented, the central axis Z is inclined by an angle $\alpha$ to the longitudinal axis L of the shaft body 4. The shaft body 4 is provided in known manner with teeth (not represented), which are distributed over its working length on the periphery, and which remove bone material when driven in the direction of longitudinal axis L.

The shaft body 4 corresponds in shape and size to an implant shaft (not shown) of a hip joint prosthesis to be equipped with a ball-and-socket. The neck part 5 is used as a slip-on mandrel for the auxiliary tool 3 and also for a test ball 6, shown in FIG. 1 by dot-dash lines and corresponding to the ball-and-socket joint, which ball is designed with a conical bore fitting on the guide portion 5b. For the precise determination of the installation position of the ball-and-socket joint to be implanted corresponding to the prevailing anatomical conditions, from a set of test balls 6 constructed with bores of varying depths, e.g. staggered by a few millimeters each time, one of the test balls can be selected in a known manner, placed on the guide portion 5b in a self-locking manner and brought together on a trial basis with the acetabulum (not represented). Accordingly by fitting trial balls 6 having bores of varying depths the final installation position of the ball-and-socket joint to be implanted (and thus the turning point on the femur) can be precisely predetermined.

The auxiliary tool 3 contains a grip part 7, which is provided at one end with a head piece 8 and at the other end with a guide bush 10 which can be placed on the end portion 5a and a coupling part 11 which can be brought together with the neck part 5. The grip part 7 may, as shown, be constructed as a curved support, which connects the guide bush 10, which can be placed on the bent neck part 5, with the head piece 8, which in the present example can be coincident with the longitudinal axis L. The head piece 8 can be provided with a spherical striking face for a tool for driving in the shaft body 4, the pressure of which is passed into the shaft body substantially in the direction of the longitudinal axis L. Bores 12 may also be provided at the grip part 7 for the attachment of a tool, e.g. a cross bar to withdraw the shaft body 4.

As can be seen in particular from FIG. 2 and 3, guide bush 10 is designed with a bore 13 housing the neck part 5, which bore comprises a cylindrical portion 13a, constructed at the shaft-side end of the guide bush as a guide face for guide portion 5a and a guide face associated with the conical guide portion 5b of the neck part 5 in the form of a corresponding conical portion 13b. According to another embodiment (not shown) a corresponding guide bush may also be provided with a bore 13 extending conically over its entire length. Grip part 7 is designed with a slip-on part 14 associated with the end of neck part 5, which covers at least a part, and as shown a half, of the cross section of the bore 13 and which with a stop face 15 extending transversally to the central axis Z can be placed on a corresponding support face 16 constructed on the front side of the neck part 5, so that the penetration depth of the neck part 5 in the guide bush 10 is restricted. As can be seen in particular from FIG. 3, the support face 16 may be formed by a recessed portion of the front face 17 of the neck part 5 and may be limited by a shoulder which forms a flank 18 extending parallel to the central axis Z. At one shoulder of the slip-on part 14 may be constructed a corresponding counter-face 20 which can be brought together with the flank 18, so that the grip part 7 can only be placed on the neck part 5 in a defined angular position.

The conical faces 5b and 13b of the neck part 5 and of the bore 13 are positioned with respect to one another in the direction of the central axis Z and with respect to the support face 16 of the neck part 5 and the stop face 15 of the grip part 5 so that when the grip part 7 is placed on support face 16, the pressure to be transferred to the shaft body 4 for the purpose of driving it in is substantially introduced via the support face 16 and the neck part 5 is guided in the bore 13 with a clearance which guarantees a central of the guide bush 10 on the neck part 5 and which at the same time, after attaining the maximum pressure to be transferred from the stop face 15 to the support face 16 when driving in the shaft member, permits a disengagement of the conical faces 5b and 13b without self-locking. Accordingly, damage to the conical face 5b of the neck part 5 to be equipped with one of the test bores 6 is avoided. By the forces acting on the neck part 5 when the rasp 2 is driven in, in certain cases compressed parts can be produced, which laterally protrude from the region of support face 16. In order to avoid damage to the relatively sensitive conical faces 5b and 13b by such compressed parts, as shown the end portion of the neck part 5 in the region of support face 16 can be designed with an annular load-relieving groove 21, by which such compressed parts are contained and can be kept away from the conical faces 5b and 13b.

Coupling part 11 is designed as a single-piece component, in the form of a detent pawl, which is pivoted at the grip part 7 around a pin 23 attached thereto, e.g. pressed in. The detent pawl is provided, in the manner of a two-armed angle lever, with a detent arm 24 oriented in the direction of central axis Z towards the shaft-side end of the guide bush 10 and with an operating arm 25 placed at right angles thereto. The detent arm 24 extends towards a recess 26 passing through the wall of the guide bush 10 over a part of its length and comprises a claw 27 which can be introduced through said recess into the bore 13 of the guide bush 10 and can be swivelled out of said bore. The claw 27 is designed with one flank 28 close to the stop face 15 of grip part 7 and with one flank 40 remote from the stop face 15. As shown, flank 28 is constructed in the form of a cylindrical face, the radius of curvature R of which corresponds to the distance of the flank 28 from the swivel axis A of coupling part 11. Flank 40 is constructed in the form of an oblique leading face inclined towards the end of the guide bush 10, which leading face is intended to interact with the end of the neck part 5. When placing the guide bush 10 on the neck part 5, the claw 27, which is kept under the action of a spring,—when its leading face coincides with the front side of the neck part 5—is swivelled increasingly out of a position corresponding roughly to that shown in FIG. 2 in the clockwise direction into a disengaged position in which the claw 27 can be displaced in the axial direction over the guide portion 13b until it engages in a recess 30 constructed in the neck part 30. The recess 30 comprises an undercut cylindrical counter-flank 31 curved to correspond to the flank 28 and turned towards the shaft member 4, and a counter-flank 41 inclined to correspond to flank 40. The engaged claw 27 is prevented from loosening by the interacting flanks 28 and 31 and can only be released by manual intervention. As shown, on the detent arm 24 may be provided a stop 29 which can abut the slip-on part 14, which limits the swivel region of the detent arm 24 towards the neck part 5 and thus the penetration depth of the claw 27 in the recess 30 to a predetermined degree, so that an introduction of the claw 27, which is substantially low-impact and gentle to the interacting faces, into the locking position provided inside recess 31 can be achieved.

The operating arm 25 comprises a connecting portion 32 bent roughly at right angles from the detent arm 24, which via a curved central portion 33, which in the present example is bent by an angle of approx. 160°, passes into a conically tapering end portion 34 constructed as a spring element, which under initial stress can abut a stop 35 constructed on the grip part 7 and via which the detent arm 24 can be braced against the slip-on part 14. When the grip part 7 is placed on the support face 16 and is central by the guide face 18, the claw 27 is accordingly forced under spring action into the locking position inside the recess 30 and retained. According to another embodiment, not represented, instead of the represented spring element, which is connected in one piece to the detent arm 24, a separate spring element can be provided, which acts in a corresponding manner and can be mounted between the detent arm 24 and the grip part 7.

By the detent arm 24 engaging in the locking position represented, the rasp 2 and the grip part 7 are fixed in the mutual position determined for driving in and withdrawing the rasp 2. To disengage the grip part 7 from the neck part 5, the operating arm 25 of the detent pawl can be swivelled by a corresponding finger movement by the surgeon holding the grip part in the clockwise direction in FIG. 2 so that the claw 27 is swivelled out of the locking position shown into a disengaged position outside the recess 30, which permits the grip part 7 to be raised from the neck part 5.

An alternative embodiment of the present invention is shown in FIGS. 4, 5 and 6. As shown in FIG. 4, the grip part 107 is constructed in the form of a straight support, and the guide bush 110 is designed in the form of a pot, the base of which is formed by the slip-on part 114, which in this design covers the entire cross section of the bore 113. As can be seen in particular from FIG. 5 and 6, the neck part 105 is designed with a second conical guide portion 105c adjoining the conical guide portion 105b and with a cylindrical end portion 105d, the front face of which is constructed as support face 116 and is provided with a groove-like cavity 137 passing diametrally through it. In this design, the cylindrical portion 113a of the bore 13 constructed at the shaft end of the guide bush 110 also extends over the longitudinal portion of the guide bush 110, which houses the conical guide portion 5b of the neck part 5 intended for the self-locking positioning of the test bore 6. This cylindrical portion 13a is limited by a conical portion 13c, which forms a guide face for the second conical guide portion 5c of the neck part 5 and which passes into a second cylindrical portion 13d, which forms a guide face for the end portion 5d of the neck part 5.

The guide portions 5c and 5d of the neck part 5 and the portions 13a, 13c and 13d of the bore 13 are also positioned in relation to the support face 16 or the stop face 15 so that when the guide bush 10 is placed on the support face 16 the cylindrical portion 13a of the bore 13 surrounds the conical guide portion 5b without any contact. By the cylindrical guide portions 5a and 5d and bore portions 13a and 13d a precise guidance of the guide bush 10 is guaranteed, which can be centered by the interacting conical faces 5c and 13c and can be placed in a correspondingly gentle manner on the neck part 5. In the region of the slip-on part 14 of the guide bush 10 is disposed a pin 38 diametrally passing through the bore portion 13d, e.g. forced in, which pin, with the counter flanks 20 associated with the groove flanks 18, forms a guide part, which protrudes over the stop face 15, and which can be inserted between two flanks 18 of cavity 37, which extend in the direction of central axis Z and are parallel to one another as represented. Accordingly in this design too the grip part 7 can only be placed on the neck part 5 in a single defined angular position and be locked thereto via coupling part 11.

Coupling part 11 shown in FIG. 5 and 6 is designed with a third lever arm 42 and is articulated on the grip part 7 by means of a screw 43. The third lever arm 42 is constructed as an easy to use operating handle, via which the claw 27 can be swung back by a simple gripping movement of the surgeon out of the locking position shown into the disengaged position or out of this position into the locking position. The recess 30 can be formed by a groove adapted to the width of the claw 27, e.g. milled in the neck part 5 (FIG. 3) or by a corresponding indentation passing through the neck part in the transverse direction (FIG. 6).

In the designs described, in the locking position the detent arm 24 lies inside the surrounding shell face of the guide bush 10. Accordingly a compact style for the device is achieved, which consists of few simple, easy-to-clean components and which enables in particular an effective protection of the interacting faces against the penetration of fluid and bone particles.

To sum up the invention can therefore be described as follows:

The device contains a rasp 2 corresponding to the implant shaft, which comprises a shaft body 4 which can be driven into the osseous tissue and a test bore 5 protruding therefrom and corresponding to the ball-and-socket joint, and a grip part 7, which can be coupled with the rasp 2, for driving in and withdrawing the shaft body 4. The grip part 7 contains a guide bush 10 which can be placed on the neck part 5 and a slip-on part 14 having a stop face 15 which can be placed on a front support face 16 of the neck part 5. On the grip part 7 is articulated a coupling part 11, which comprises a claw 27, which through a recess 26 in the guide sleeve 7 can engage in a recess 30 in the neck part 5 and be disengaged therefrom. With this device, which can be manufactured from simple components which are easy to keep sterile, all the stop, guide and clamping faces operational when driving in and withdrawing the shaft body 4 lie inside the enveloping shell surface of the neck part 5 and as a result are protected from contact with fluid and bone particles.

We claim:

1. A rasp for preparing a tubular bone for the insertion of an implant shaft of the type having an artificial ball-and-socket joint, the device comprising:

a cutter sized and shaped to correspond to the implant shaft and having a shaft body with a longitudinal axis, the shaft body being insertable into the bone in the direction of the longitudinal axis, the cutter further comprising a neck extending from the shaft body and defining a front support face remote from the shaft body, the neck having a smaller transverse cross-sectional area than the shaft body and being adapted for receiving a test ball-corresponding to the ball-and-socket joint; and a grip having a guide bush that defines a bore for receiving a proximal portion of the neck of the cutter, the grip having a locking mechanism detachably connected to the neck and adjustably mounted on the grip, the locking mechanism being movable between open and closed positions for unlocking and locking the neck to the grip, the grip further defining a stop face for abutting against the front support face of the neck and limiting a penetration depth of the neck within the guide bush, the stop face being positioned to space the guide bush a distance away from the shaft body, whereby an insertion force applied to the grip is directly applied by the grip only to the neck within the guide bush.

2. The rasp of claim 1 wherein the neck defines a central axis and a distal cylindrical guide portion spaced from the shaft body, the cylindrical guide portion being insertable into the guide bush of the grip, the neck further defining a proximal conical guide portion contiguous with the cylindrical guide portion and being adapted to cooperate with a conical bore of the test ball, the conical guide portion tapering in relation to the central axis, the bore of the guide bush defining a distal cylindrical guide face corresponding to the distal cylindrical guide portion of the neck, the guide portions and the guide face being positioned with respect to one another and with respect to the support face of the neck and the stop face of the grip such that the conical guide portion is removably secured within the bore when the shaft body has been driven into the tubular bone with the grip.

3. The rasp of claim 2 wherein the guide bush further defines a conical guide face corresponding to the conical guide portion of the neck.

4. The rasp of claim 2 wherein the cylindrical guide face of the bore extends over a longitudinal portion of the guide bush to circumscribe the conical guide portion of the neck.

5. The rasp of claim 1 wherein the neck of the cutter comprises a recess and the locking mechanism comprises a detent pawl pivotable on the grip about a pivot axis, the detent pawl having a claw movable between a locking position within the recess of the neck and a disengaged position exterior to said recess.

6. The rasp of claim 5 wherein the detent pawl further comprises a spring element and the grip includes a stop, the spring element abutting the stop when the claw is in the locking position to secure the claw in the locking position.

7. The rasp of claim 6 wherein the detent pawl and the spring element are integral.

8. The rasp of claim 5 wherein the guide bush defines a recess, the detent pawl being disposed within the guide bush recess.

9. The rasp of claim 5 wherein the claw of the detent pawl comprises a flank facing the stop face of the grip, the recess of the neck defining a counter flank corresponding to and cooperating with the flank of the claw.

10. The rasp of claim 5 wherein the claw of the detent pawl comprises a flank remote from the stop face of the grip and constructed in the form of an oblique leading face, the flank of the claw interacting with an end of the neck when the neck is received within the guide bush, wherein the claw pivots towards the disengaged position when the guide bush is positioned over the neck of the cutter such that the claw engages the recess of the neck when the stop face of the grip engages the front support face of the neck.

11. A rasp for preparing a tubular bone for the insertion of an implant shaft of the type having an artificial ball-and-socket joint, the device comprising:

a cutter sized and shaped to correspond to the implant shaft and having a shaft body with a longitudinal axis, the shaft body being insertable into the bone in the direction of the longitudinal axis, the cutter further comprising a neck extending from the shaft body and defining a front support face remote from the shaft body, the neck being adapted for receiving a test ball corresponding to the ball-and-socket joint; and a grip having a guide bush that defines a bore for receiving a proximal portion of the neck of the cutter, the grip having a locking mechanism detachably connected to the neck and adjustably mounted on the grip, the locking mechanism being movable between open and closed positions for unlocking and locking the neck to the grip, the grip further defining a stop face for abutting against the front support face of the neck and limiting a penetration depth of the neck within the guide bush, the stop face being positioned to space the guide bush a distance away from the shaft body;

wherein the neck defines a central axis and a distal cylindrical guide portion spaced from the shaft body, the cylindrical guide portion being insertable into the guide bush of the grip, the neck further defining a proximal conical guide portion contiguous with the cylindrical guide portion and being adapted to cooperate with a conical bore of the test ball, the conical guide portion tapering in relation to the central axis, the bore of the guide bush defining a distal cylindrical guide face corresponding to the distal cylindrical guide portion of the neck, the guide portions and the guide face being positioned with respect to one another and with respect to the support face of the neck and the stop face of the grip such that the conical guide portion is removably secured within the bore when the shaft body has been driven into the tubular bone with the grip;

wherein the cylindrical guide face of the bore extends over a longitudinal portion of the guide bush to circumscribe the conical guide portion Of the neck;

wherein the neck comprises a second conical guide portion contiguous with the first conical guide portion and the bore of the guide bush defines a second conical guide face corresponding to said second conical guide portion.

12. The rasp of claim 11 wherein the neck comprises a proximal cylindrical end portion contiguous with the second conical guide portion and the bore of the guide bush defines a second cylindrical guide face corresponding to said cylindrical end portion.

13. A rasp for preparing a tubular bone for the insertion of an implant shaft of the type having an artificial ball-and-socket joint, the device comprising:

a cutter sized and shaped to correspond to the implant shaft and having a shaft body with a longitudinal axis, the shaft body being insertable into the bone in the direction of the longitudinal axis, the cutter further comprising a neck extending from the shaft body and defining a front support face remote from the shaft body, the neck being adapted for receiving a test ball corresponding to the ball-and-socket joint; and a grip having a guide bush that defines a bore for receiving a proximal portion of the neck of the cutter, the grip having a locking mechanism detachably connected to the neck and adjustably mounted on the grip, the locking mechanism being movable between open and closed positions for unlocking and locking the neck to the grip, the grip further defining a stop face for abutting against the front support face of the neck and limiting a penetration depth of the neck within the quids bush, the stop face being positioned to space the quids bush a distance away from the shaft body;

wherein the grip further comprises a slip-on-part extending across at least a portion of the cross-section of the bore of the guide bush, the slip-on-part comprising the stop face and a counter-face, the neck comprising a guide face transverse to the support face and extending in the direction of the central axis of the neck, the guide face engaging the counter-face of the slip-on-part.

14. The rasp of claim 13 wherein the support face of the neck is constructed at a recessed portion of the front face, the guide face being constructed at a shoulder portion of the neck and the counter face being constructed on a corresponding shoulder portion of the slip-on-part.

15. The rasp of claim 13 wherein the support face of the neck defines a cavity having a flank, the guide face of the neck being formed on the flank, the slip-on-part comprising a pin which is insertable into the cavity, the counter face of the slip-on-part being formed on the pin.

16. A rasp for preparing a tubular bone for the insertion of an implant shaft of the type having an artificial ball-and-socket joint, the device comprising:

- a cutter sized and shaped to correspond to the implant shaft and having a shaft body with a longitudinal axis, the shaft body being insertable into the bone in the direction of the longitudinal axis, the cutter further comprising a neck extending from the shaft body and defining a front support face remote from the shaft body, the neck being adapted for receiving a test ball corresponding to the ball-and-socket joint; and
- a grip having a guide bush that defines a bore for receiving a proximal portion of the neck of the cutter, the grip having a locking mechanism detachably connected to the neck and adjustably mounted on the grip, the locking mechanism being movable between open and closed positions for unlocking and locking the neck to the grip, the grip further defining a stop face for abutting against the front support face of the neck and limiting a penetration depth of the neck within the guide bush, the stop face being positioned to space the guide bush a distance away from the shaft body;
- wherein the neck of the cutter comprises a recess and the locking mechanism comprises a detent pawl pivotable on the grip about a pivot axis, the detent pawl having a claw movable between a locking position within the recess of the neck and a disengaged position exterior to said recess, the claw of the detent pawl comprising a flank facing the stop face of the grip, the recess of the neck defining a counter flank corresponding to and cooperating with the flank of the claw;

wherein the flank of the claw and the counter flank of the neck are constructed in the form of an undercut cylindrical face having a radius of curvature which corresponds to a distance between said flank and the pivot axis of the detent pawl.

17. A rasp for preparing a tubular bone for the insertion of an implant shaft of the type having an artificial ball-and-socket joint, the device comprising:

- a cutter sized and shaped to correspond to the implant shaft and having a shaft body with a longitudinal axis, the shaft body being insertable into the bone in the direction of the longitudinal axis, the cutter further comprising a neck extending from the shaft body along a central axis transverse to the longitudinal axis and defining a front support face remote from the shaft body, the neck defining a distal portion contiguous with the shaft body and a proximal portion contiguous with the distal portion, the distal and proximal portions of the neck having smaller transverse cross-sectional areas than the shaft body; and
- a grip having a guide bush that defines a bore for receiving the proximal portion of the neck of the cutter, the grip defining a stop face for abutting against the front support face of the neck when the proximal portion of the neck is positioned within the bore of the guide bush, the stop face and the front support face being positioned such that the distal portion of the neck remains exterior to the bore of the guide bush when the stop face abuts against the front support face such that the guide bush is spaced away from the shaft body of the cutter, whereby an insertion force applied to the grip is directly applied by the grip only to the neck within the guide bush.

* * * * *